United States Patent [19]

Felder et al.

[11] 4,251,341

[45] Feb. 17, 1981

[54] PHOTOINITIATORS FOR UV-CURABLE SYSTEMS

[75] Inventors: Louis Felder, Basel; Rudolf Kirchmayr, Aesch; Andreas Schmidt, Reinach, all of Switzerland

[73] Assignee: Ciba-Geigy Corporation, Ardsley, N.Y.

[21] Appl. No.: 48,970

[22] Filed: Jun. 15, 1979

Related U.S. Application Data

[62] Division of Ser. No. 814,366, Jul. 11, 1977, abandoned.

[30] Foreign Application Priority Data

Jul. 15, 1976 [CH] Switzerland ............... 9087/76

[51] Int. Cl.³ .................... C08F 2/46; C08F 4/00
[52] U.S. Cl. .................. 204/159.24; 106/20; 106/23; 106/25; 204/159.14; 204/159.15; 204/159.19; 204/159.22; 204/159.23
[58] Field of Search ............ 204/159.14, 159.15, 204/159.19, 159.22, 159.23, 159.24, 160.1; 106/20, 23, 25; 260/346.22, 347.2

[56] References Cited

U.S. PATENT DOCUMENTS

| | | | |
|---|---|---|---|
| 3,458,548 | 7/1969 | Carlson | 260/590 D |
| 3,536,661 | 10/1970 | Hagemeyer, Jr. et al. | 260/590 D |
| 3,707,302 | 1/1974 | Ijichi et al. | 204/159.23 |
| 3,801,329 | 4/1974 | Sandner et al. | 204/159.23 |
| 3,966,573 | 6/1976 | Bean | 204/159.23 |
| 3,998,712 | 12/1976 | Hickmann et al. | 260/590 D |
| 4,071,424 | 1/1978 | Dart et al. | 204/159.19 |
| 4,131,529 | 12/1978 | Osterloh et al. | 204/159.19 |

FOREIGN PATENT DOCUMENTS 925445  1/1961  United Kingdom ............ 260/590

*Primary Examiner*—J. Ziegler
*Attorney, Agent, or Firm*—Harry Falber

[57] ABSTRACT

Dialkoxy-acetyl derivatives of aromatic compounds are photosensitizers for the curing of photopolymerisable systems. They can be synthesized from aromatic acetyl compounds(aryl methyl ketones) by reaction with nitrosyl chloride and the corresponding alkanol. Examples of photopolymerizable systems are coatings or printing inks on the basis of unsaturated polyesters or acrylic compounds.

13 Claims, No Drawings

PHOTOINITIATORS FOR UV-CURABLE SYSTEMS

This is a divisional of application Ser. No. 814,366, filed July 11, 1977, now abandoned.

The invention relates to new photoinitiators for the photopolymerisation of unsaturated compounds. It concerns new dialkoxyacetyl derivatives of aromatic compounds.

Photochemical polymerisation processes have attained considerable importance in industry, especially in such cases where thin layers have to be cured within a short time, for example in the curing of lacquer coatings or in the drying of printing inks. Compared with conventional curing processes, the UV irradiation process in the presence of photoinitiators has a number of advantages, of which the most significant is probably the high rate of photo-curing. The rate is greatly dependent on the photoinitiator used, and there has been no lack of attempts to replace the conventional initiators by even better and more effective compounds. Among the most effective photoinitiators are derivatives of benzoin, particularly benzoin ethers such as are described for example in British Patent Specifications Nos. 1,213,498, 1,254,231 and 1,156,460 or in Swiss Pat. No. 511,902; and also dialkoxyacetophenones of the formula

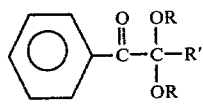

wherein R represents alkyl or aryl, and R' represents hydrogen, alkyl, aryl or cycloalkyl, such as are described in U.S. Pat. No. 3,715,293.

Disadvantages associated with these known photoinitiators include in some cases inadequate stability of photopolymerisable systems mixed with such initiators to storage in the dark. Some benzoin derivatives tend to cause yellowing of the cured systems. Other initiators possess insufficient reactivity, which is reflected in relatively long curing times; or their solubility in the photopolymerisable systems is too low; or they are rapidly deactivated by atmospheric oxygen. There is in industry therefore a need for photoinitiators which are readily soluble in the substrate, which initiate photopolymerisation more rapidly whilst having good stability to storage in the dark, and which produce a polymer yield per unit of time greater than that produced by the known photoinitiators. The use of such improved photoinitiators would lead to a better utilisation of the expensive industrial UV irradiation equipment.

It has been found that compounds of the following formulae I and II possess as photoinitiators the properties required, and do not have the disadvantages described, or have them to an extent that is far less than in the case of the known photoinitiators. These new compounds are characterised by the general formulae I or II

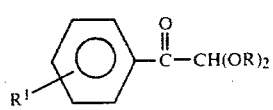

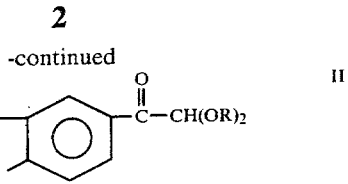

wherein
X represents oxygen or sulphur,
R represents alkyl having 1–4 C atoms, alkoxyalkyl having 3–6 C atoms, $C_1$–$C_4$-alkyl—$OCH_2CH_2OCH_2CH_2$—, or chloroalkyl having 2–3 C atoms,
$R^1$ represents alkyl having 1–4 C atoms, alkoxy or alkylthio having 1–4 C atoms, cycloalkyl having 5–6 C atoms, aralkyl having 7–9 C atoms, chlorine, bromine, a group of the formula —CO—CH(OR)$_2$, or a group of the formula

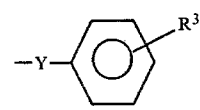

Y represents a direct bond, oxygen or sulphur,
$R^2$ represents hydrogen, alkyl having 1–4 C atoms, alkoxy or alkylthio having 1–4 C atoms, chlorine, bromine or a group —CO—CH(OR)$_2$, and
$R^3$ represents hydrogen, alkyl having 1–4 C atoms, alkoxy having 1–4 C atoms, chlorine, bromine, alkoxycarbonyl having 2–5 C atoms, or a group of the formula —CO—CH(OR)$_2$.

Compounds particularly concerned are those of the formula I or II

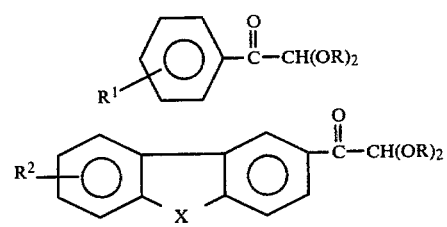

wherein
X represents oxygen or sulphur,
R represents alkyl having 1–4 C atoms, alkoxyalkyl having 3–6 C atoms or chloroalkyl having 2–3 C atoms,
$R^1$ represents alkyl having 1–4 C atoms, alkoxy or alkylthio having 1–4 C atoms, cycloalkyl having 5–6 C atoms, aralkyl having 7–9 C atoms, chlorine, bromine, a group of the formula —CO—CH(OR)$_2$ or a group of the formula

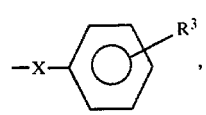

$R^2$ represents hydrogen, alkyl having 1–4 C atoms, alkoxy or alkylthio having 1–4 C atoms, chlorine, bromine or a group —CO—CH(OR)$_2$, and
$R^3$ represents hydrogen, alkyl having 1–4 C atoms, alkoxy having 1–4 C atoms, chlorine, bromine, alkoxycarbonyl having 2–5 C atoms, or a group of the formula —CO—CH(OR)$_2$.

R, R$^1$, R$^2$ or R$^3$ as alkyl can represent methyl, ethyl, propyl or butyl, and the propyl and butyl group can be straight-chain or branched-chain.

As alkoxyalkyl, R can represent for example 2-methoxyethyl, 2-butoxyethyl or 2-ethoxypropyl; as chloroalkyl, R can represent chloroethyl or chloropropyl.

R$^1$, R$^2$ or R$^3$ as alkoxy can represent, for example, methoxy, isopropoxy or t-butoxy. As alkylthio, R$^1$ and R$^2$ can represent for example ethylthio or butylthio.

If R$^1$ represents cycloalkyl, it can be for example cyclopentyl or cyclohexyl. If R$^1$ represents aralkyl, it can be for example benzyl or phenylethyl.

R$^3$ can also represent alkoxycarbonyl, for example methoxycarbonyl or ethoxycarbonyl.

Preferred compounds of the formula I are those wherein R represents alkyl having 1–4 C atoms or alkoxyalkyl having 3–4 C atoms, R$^1$ represents alkyl having 1–4 C atoms, alkoxy having 1–4 C atoms, chlorine, a group of the formula

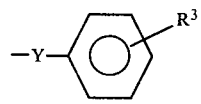

or a group of the formula —CO—CH(OR)$_2$, Y represents a direct bond, oxygen or sulphur, and R$^3$ represents H, CH$_3$, Cl or —CO—CH(OR)$_2$; particularly however those compounds of the formula I wherein R represents alkyl having 1–4 C atoms, and R$^1$ represents methyl, methoxy, chlorine, a group of the formula —CO—CH(OR)$_2$, or a group of the formula

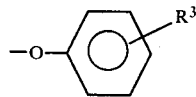

wherein R$^3$ represents hydrogen or —CO—CH(OR)$_2$.

Compounds of the formula I which are also preferred are those wherein R represents alkyl having 1–4 C atoms, and R$^1$ represents methyl, methoxy, —CO—CH(OR)$_2$, or a group of the formula

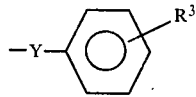

wherein R$^3$ represents hydrogen or —CO—CH(OR)$_2$, and Y represents a direct bond, oxygen or sulphur.

Preferred compounds of the formula II are those wherein X represents oxygen or sulphur, R represents alkyl having 1–4 C atoms or alkoxyalkyl having 3–4 C atoms, and R$^2$ represents hydrogen, alkyl having 1–4 C atoms, alkoxy having 1–4 C atoms, chlorine or —CO—CH(OR)$_2$. Particularly preferred are those compounds of the formula II wherein X represents oxygen, R represents alkyl having 1–4 C atoms, and R$^2$ represents hydrogen or —CO—CH(OR)$_2$. Further preferred compounds of the formula II are those wherein X represents oxygen or sulphur, R represents alkyl having 1–4 C atoms, and R$^2$ represents hydrogen.

Individual examples of compounds of the formula I are: 4-(dimethoxyacetyl)-toluene, 4-(diethoxyacetyl)-isopropylbenzene, 4-(dibutoxyacetyl)-tert.-butylbenzene, 4-methoxy-α,α-diethoxy-acetophenone, 2-ethoxy-α,α-diethoxy-acetophenone, 4-(dimethoxyacetyl)-chlorobenzene, 4-(dipropoxyacetyl)-bromobenzene, 4-(dimethoxyacetyl)-diphenyl oxide, 4-methyl-4'-(dimethoxyacetyl)-diphenyl oxide, 4-chloro-4'-(diisopropoxyacetyl)-diphenyl oxide, 4-(diethoxyacetyl)-diphenyl sulphide, 3-methylthio-α,α-dimethoxy-acetophenone, 4-tert.-butyl-α,α-di-(2-methoxyethoxy)-acetophenone, 4-[di-(2-chloroethoxy)-acetyl]-chlorobenzene, 1,4-bis-(dimethoxyacetyl)-benzene, 1,3-bis-(diisopropoxyacetyl)-benzene, 4,4'-bis-(diethoxyacetyl)-diphenyl oxide and 4,4'-bis-(dimethoxyacetyl)-diphenyl sulphide.

Examples of the compounds of the formula II are: 2-(dimethoxyacetyl)-diphenylene oxide, 2,8-bis-(diethoxyacetyl)-diphenylene oxide, 3-methyl-8-(diethoxyacetyl)-diphenylene oxide, 2-chloro-8-(dibutoxyacetyl)-diphenylene oxide, 2-methoxy-8-(dimethoxyacetyl)-diphenylene sulphide and 2,8-bis-(diisopropoxyacetyl)-diphenylene sulphide.

The compounds of the formulae I and II can be produced, by methods known per se, from the corresponding acetylbenzenes of the formula Ia

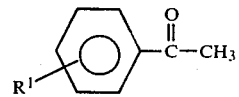

or from the acetyl-dibenzofurans or acetyl-dibenzothiophenes of the formula IIa

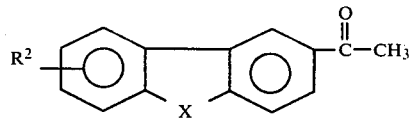

For example, the acetyl compounds can be converted by means of selenium dioxide into the corresponding α-keto aldehydes, as is described, e.g., in Organic Synthesis, Coll. Vol. II (1943), page 509. The α-keto aldehydes can be acetalised, in a manner known per se, selectively on the aldehyde group.

Another method is the reaction of the acetyl compound Ia or IIa with nitrosyl chloride in the presence of an alcohol of the formula ROH. This method is described in J.Org.Chem. 26 (1961), 3755. The production of certain compounds of the formula I or II is further illustrated in the Examples to be given later on in the text.

The photoinitiators according to the invention can be used for photopolymerisation of polymerisable unsaturated compounds or systems which contain such compounds.

Examples of such compounds are unsaturated monomers, such as esters of acrylic or methacrylic acid, e.g. methyl acrylate, ethyl acrylate, n- or tert.-butylacrylate, isooctyl acrylate or hydroxyethyl acrylate, methyl methacrylate or ethyl methacrylate, ethylene diacrylate, neopentyl diacrylate, trimethylolpropane tris-acrylate, pentaerythritol tetraacrylate or pentaerythritol tris-acrylate; acrylonitrile, methacrylonitrile, acrylamide, methacrylamide and N-substituted (meth)acrylamides; vinyl esters, such as vinyl acetate, vinyl propionate, vinyl acrylate or vinyl succinate; other vinyl compounds, such as vinyl ether, styrene, alkylstyrenes, halogenostyrenes, divinylbenzene, vinylnaphthalene, N-vinylpyrrolidone, vinyl chloride or vinylidene chloride; and allyl compounds, such as diallyl phthalate, diallyl maleate, triallyl isocyanurate, triallyl phosphate or ethylene glycol diallyl ether, and the mixtures of such unsaturated monomers.

Further photopolymerisable compounds are unsaturated oligomers of polymers and their mixtures with unsaturated monomers. These include thermoplastic resins which contain unsaturated groups, such as fumaric acid ester or allyl groups or acrylate or methacrylate groups. In most cases, these unsaturated groups are bonded to the main chain of these linear polymers via functional groups. Mixtures of oligomers with monounsaturated and polyunsaturated monomers are of great importance. Examples of such oligomers are unsaturated polyesters, unsaturated acrylic resins and isocyanate-modified or epoxide-modified acrylate oligomers. Examples of polyunsaturated compounds are, above all, the acrylates of diols and polyols, for example hexamethylene diacrylate or pentaerythritol tetraacrylate. Acrylates, such as butyl acrylate, phenyl acrylate, benzyl acrylate, 2-ethylhexyl acrylate or 2-hydroxyethyl acrylate, are also preferred as monounsaturated monomers. The means of varying the consistency of the unpolymerised mixture and the plasticity of the polymerised resin is provided by the choice from the different representatives of the three components.

In addition to these three-component mixtures, particularly two-component mixtures play an important part in the case of polyester resins. These mixtures usually consist of an unsaturated polyester and a vinyl compound. The unsaturated polyesters are oligomeric esterification products of at least one unsaturated dicarboxylic acid, such as maleic acid, fumaric acid or citraconic acid, and in most cases at least one saturated dicarboxylic acid, for example phthalic acid, succinic acid, sebacic acid or isophthalic acid, with glycols, such as ethylene glycol, propane-1,2-diol, di- or tri-ethylene glycol or tetramethylene glycol, and in most cases monocarboxylic acids and monoalcohols are concomitantly used for modification. These unsaturated polyesters are usually dissolved in a vinyl or allyl compound, and styrene is preferably used for this purpose.

Photopolymerisable systems, such as are used for the various purposes, contain in most cases a number of other additives in addition to the photopolymerisable compounds and the photoinitiator. Thus, it is often customary to add thermal inhibitors, which are primarily intended to provide protection against premature polymerisation during the preparation of the systems when the components are being mixed. Compounds used for this purpose are, for example, hydroquinone, p-methoxyphenyl, $\beta$-naphthylamine or $\beta$-naphthols. Furthermore, small amounts of UV absorbers, such as those of the benztriazole or benzophenone type, can be added without the reactivity of the photoinitiators being noticeably impaired.

Copper compounds, such as copper naphthenate, copper stearate or copper octoate, phosphorus compound, such as triphenylphosphine, tributylphosphine, triethyl phosphite, triphenyl phosphite or tribenzyl phosphate, quaternary ammonium compounds, such as tetramethylammonium chloride or trimethylbenzylammonium chloride, or hydroxylamine derivatives, such as N-diethylhydroxylamine, can be added in order to increase the stability to storage in the dark. Furthermore, the photopolymerisable systems can contain chain-propagating agents, such as N-methyldiethanolamine, triethanolamine or cyclohexene.

In order to exclude the inhibiting action of atmospheric oxygen, paraffin or similar waxy substances are frequently added to the photo-curable systems. Because of their lack of solubility in the polymer, these substances float to the surface at the start of polymerisation and form a transparent surface layer which prevents the admission of air. Atmospheric oxygen can also be deactivated by the introduction of auto-oxidisable groups, for example, allyl groups, into the resin to be cured.

Depending on their intended use, photopolymerisable systems can contain fillers, such as silica, talc or gypsum, pigments, dyes, fibres, agents which impart thixotropic properties or flow auxiliaries.

Photo-curing is of great importance in the case of printing inks since the drying time of the binder is a decisive factor determining the rate at which graphic products are produced and should be of the order of size of fractions of a second. The initiators according to the invention are also very suitable for photo-curable systems for the manufacture of printing plates. In this case, mixtures of soluble linear polyamides with photopolymerisable monomers, for example acrylamides, and a photoinitiator are generally used. Films or plates made from these systems are exposed via the negative (or positive) of the print original, and the uncured parts are then eluted with a solvent.

A further field of application of UV-curing is metal coating, for example when lacquer-coating sheet metal for tubes, tins or bottle closures.

Examples of the UV-curing of paper coatings are the colourless lacquer coating of labels, record sleeves or book covers.

For the indicated fields of application, the compounds of the formulae I and II are advantageously used in amounts of 0.1 to 20% by weight, and preferably in amounts of about 0.5 to 5% by weight, relative to the photopolymerisable system. In this context, system means the mixture of the photopolymerisable compound and the photoinitiator, together with the fillers and additives, which is used in the particular application.

The addition of the photoinitiators to the photopolymerisable systems is generally effected by simple stirring-in, since most of these systems are liquid or readily soluble. In most cases a solution of the initiators according to the invention is obtained, in consequence of which their homogeneous distribution and the transparency of the polymers are ensured.

Polymerisation is effected by the known methods of photopolymerisation by irradiation with light which is rich in shortwave radiation. Examples of suitable sources of light are medium pressure, high pressure and low pressure mercury lamps and also superactinic fluorescent tubes which have emission maxima in the range between 250 and 400 nm.

Production and use of compounds of the formulae I and II are described in more detail in the following Examples. In these Examples, parts denote parts by weight, percentages denote percent by weight, and the temperature is given in degrees Centigrade.

EXAMPLE 1

1,4-Bis-(diethoxyacetyl)-benzene 10 g (0.061 mole) of 1,4-diacetylbenzene is suspended in 185 ml of ethanol, and 24.4 g (0.375 mole) of nitrosyl chloride is introduced at room temperature, with good stirring, into the suspension. The mixture is subsequently heated for 2½ hours at 63°, and the excess ethanol is distilled off in a water-jet vacuum until the internal temperature has reached 60°. 81 ml of 2 N sodium hydroxide solution is added to the reaction mixture, and this is then refluxed for 90 minutes. After cooling, extraction is performed three times with ether, and the organic phase is completely concentrated by evaporation. There is obtained 1,4-bis-(diethoxyacetyl)-benzene as yellow-brown oil.

Analysis: calculated: C, 63.89%; H, 7.75%. found: C, 62.64%; H, 8.00%.

EXAMPLE 2 p-Methoxy-α,α-diethoxyacetophenone

Starting with p-methoxyacetophenone, there is obtained, by a procedure analogous to that described in Example 1, p-methoxy-α,α-diethoxy-acetophenone. This compound boils at 109°–112°/0.35–0.38 mm.

Analysis: calculated: C, 65.53%; H, 7.61%. found: C, 65.89%; H, 7.57%.

EXAMPLE 3

4-(Dimethoxyacetyl)-toluene

From p-methylacetophenone is obtained, using the procedure described in Example 1, 4-(dimethoxyacetyl)-toluene, which boils at 142°–143°/9 mm.

Analysis: calculated: C, 70.24%; H, 8.6%. found: C, 70.1%; H, 8.1%.

EXAMPLE 4

2-(Diethoxyacetyl)-diphenylene oxide 10.7 g (0.05 mole) of 2-acetyl-diphenylene oxide is placed into 200 ml of ethanol, and with good stirring and with cooling to room temperature there is added 10 g (0.15 mole) of nitrosyl chloride. The reaction mixture is slowly heated to 60° and held at this temperature for 2½ hours. The ethanol is then distilled off at 60° under reduced pressure. 100 ml of 2 N sodium hydroxide solution is added to the residue and refluxing is performed for 90 minutes. After cooling, extraction is carried out 3 times with ether, and the organic phase is completely concentrated by evaporation. The dark oil remaining is purified through a silica gel column with toluene as the eluant to obtain 2-(diethoxyacetyl)-diphenylene oxide as yellow-brown oil.

Analysis: calculated: C, 72.47%; H, 6.08%. found: C, 73.22%; H, 6.63%.

EXAMPLE 5

4-(Dimethoxyacetyl)-diphenyl oxide 5.6 g (0.085 mole) of NOCl is introduced at 5°–10° into 6.3 g (0.03 mole) of 4-acetyl-diphenyl oxide in 80 ml of methanol. After removal of the cooling bath, the temperature of the reaction mixture rises to 30° with the evolution of HCl. After 3 hours of further stirring at room temperature, the reaction mixture is concentrated by evaporation and extracted with ether. The ether solution is washed with NaHCO$_3$ solution and water, dried and concentrated by evaporation. The crude product (7.3 g) obtained as oil is chromatographed on a silica gel column with CH$_2$Cl$_2$.

$C_{16}H_{16}O_4$: calculated: C, 70.58; H, 5.92; O, 23.50%. (272.30): found: C, 69.0; H, 5.8; O, 23.3%.

EXAMPLE 6

4,4'-Bis-(dimethoxyacetyl)-diphenyl oxide 5 g (0.02 mole) of 4,4'-diacetyl-diphenyl oxide is placed into 80 ml of methanol, and at 0°–5° there is introduced 7.2 g (0.11 mole) of NOCl. After removal of the cooling bath, the temperature of the reaction mixture rises to 35°. After 3 hours of further stirring, the reaction mixture is concentrated by evaporation and the residue is taken up in ether. The ether solution is washed with NaHCO$_3$ solution and water, dried and concentrated by evaporation. The crude product obtained is chromatographed on a silica gel column with ethyl acetate/hexane 2:3.

$C_{20}H_{22}O_7$: calculated: C, 64.16; H, 5.93; O, 29.92%. (374.39): found: C, 64.7; H, 5.7; O, 29.7%.

EXAMPLE 7

4,4'-Bis-(diethoxyacetyl)-diphenyl 3 g (0.013 mole) of 4,4'-diacetyl-diphenyl is placed into 50 ml of ethanol (suspension), and at 0°–5° there is introduced 5.2 g (0.08 mole) of NOCl. After removal of the cooling bath, the temperature of the reaction mixture rises to 40° with the evolution of HCl, with a clear solution being formed. After 3 hours' further stirring at room temperature, the reaction mixture is concentrated by evaporation and the residue is taken up in ether. The ether solution is washed with NaHCO$_3$ solution and water, dried and concentrated by evaporation. The crude product obtained as oil is chromatographed on a silica gel column with ethyl acetate/hexane 1:4.

Yield of product (oil): 1.5 g (27%).

$C_{24}H_{30}O_6$: calculated: C, 69.55; H, 7.30; O, 23.16%. (414.5): found: C, 69.5; H, 7.2; O, 23.3%.

EXAMPLE 8

4-(Diethoxyacetyl)-diphenyl oxide 6.7 g (0.1 mole) of NOCl is introduced at 5°–10° into 6.3 g (0.03 mole) of 4-acetyl-diphenyl oxide in 80 ml of ethanol. After removal of the cooling bath, the temperature of the reaction solution rises to 35° with the evolution of HCl. After 3 hours of further stirring at room temperature, the reaction solution is concentration by evaporation and the residue is taken up in ether. The ether solution is washed with NaHCO$_3$ solution and water, dried and concentrated by evaporation. The crude product (7.5 g) obtained as oil is chromatographed on a silica gel column with CH$_2$Cl$_2$.

Yield of product (oil): 4.8 g (43%).

$C_{18}H_{20}O_4$: calculated: C, 71.98; H, 6.71; O, 21.31%. (300.35): found: C, 72.0; H, 6.7; O, 21.6%.

EXAMPLE 9

4-(Di-isopropoxyacetyl)-diphenyl oxide 9.8 g (0.15 mole) of NOCl is introduced at 5°–10° into 12.6 g (0.06 mole) of 4-acetyl-diphenyl ether in 160 ml of isopropanol. After removal of the cooling bath, the temperature of the reaction mixture rises with the evolution of HCl; it is still slightly cooled so that the temperature of the reaction mixture does not exceed 35°. After subsequent stirring for 3 hours at room temperature, the reaction solution is concentrated by evaporation and the residue is taken up in ether. The ether solution is washed with NaHCO$_3$ solution and water, dried and concentrated by evaporation. The crude product obtained as oil is chromatographed on a silica gel column with CH$_2$Cl$_2$. Yield: 6.2 g (32%) of product in the form of oil, which crystallises on standing, m.p. 43°–45°.

C$_{20}$H$_{24}$O$_4$: calculated: C, 73.15; H, 7.37; O, 19.49%. (328.41): found: C, 72.8; H, 7.2; O, 19.6%.

EXAMPLE 10

4,4'-Bis-(diethoxyacetyl)-diphenyl oxide 10 g (0.04 mole) of 4,4'-diacetyl-diphenyl oxide is placed into 160 ml of ethanol (suspension), and at 0°–5° there is introduced 13 g (0.2 mole) of NOCl; and a solution is formed. After removal of the cooling bath, the temperature of the reaction mixture rises to 35° with the evolution of HCl. After subsequent stirring for 3 hours at room temperature, the reaction solution is concentrated by evaporation, and the residue is taken up in ether. The ether solution is washed with NaHCO$_3$ solution and water, dried and concentrated by evaporation. The crude product obtained as oil (15 g) is chromatographed on a silica gel column once with CH$_2$Cl+1% of methanol and once with ethyl acetate/hexane 1:4.

Yield of product (oil): 3.5 g (20%).

C$_{24}$H$_{30}$O$_7$: calculated: C, 66.96; H, 7.03; O, 26.02%. (430.50): found: C, 66.7; H, 6.9; O, 26.3%.

EXAMPLE 11

4,4'-Bis-(di-iso-propoxyacetyl)-diphenyl oxide 15 g (0.06 mole) of 4,4'-diacetyl-diphenyl oxide is placed into 240 ml os iso-propanol (suspension), and at 0°–10° there is introduced 19.5 g (0.3 mole) of NOCl, with a solution being formed. After removal of the cooling bath, the temperature of the reaction solution rises with the evolution of HCl; by slight cooling, a temperature rise to above 35° is prevented. After subsequent stirring for 3 hours at room temperature, the reaction solution is concentrated by evaporation and the residue is taken up in ether. The ether solution is washed with NaHCO$_3$ solution and water, dried and concentrated by evaporation. The crude product obtained as oil (17 g) is chromatographed on a silica gel column with ethyl acetate/hexane 1:4. Yield of product (oil): 4.2 g (14.4%).

C$_{28}$H$_{38}$O$_7$: calculated: C, 69.11; H, 7.87%. (486.61): found: C, 68.6; H, 7.4%.

EXAMPLE 12

4-(Diethoxyacetyl)-diphenyl sulphide 11.4 g (0.05 mole) of 4-acetyl-diphenyl sulphide is placed into 140 ml of ethanol (suspension), and at 5°–10° there is introduced 8.3 g (0.125 mole) of NOCl, and a yellow reaction solution is formed. After removal of the cooling bath, the temperature of the reaction solution rises with the evolution of HCl; the temperature is kept below 35° by slight cooling. After subsequent stirring for 4 hours at room temperature, the reaction solution is concentrated by evaporation, and the residue is taken up in ether. The ether solution is washed with NaHCO$_3$ solution and water, dried and then concentrated by evaporation. The crude product is chromatographed on a silica gel column with CH$_2$Cl$_2$.

Yield of product (oil): 6.8 g (43%).

C$_{18}$H$_{20}$O$_3$S: calculated: C, 68.33; H, 6.37; O, 15.17 S, 10.13%. (316.42): found: C, 68.1; H, 6.4; O, 15.6 S, 10.1%.

EXAMPLE 13

4,4'-Bis-(diethoxyacetyl)-diphenyl sulphide 13 g (0.2 mole) of NOCl is introduced at 5°–10° into 10.8 g (0.04 mole) of 4,4'-diacetyl-diphenyl sulphide suspended in 160 ml of ethanol. After removal of the cooling bath, the temperature of the reaction solution rises with the evolution of HCl; the temperature is maintained below 35° by slight cooling. After subsequent stirring for a further 4 hours at room temperature, the reaction solution is concentrated by evaporation and the residue is taken up in ether. The ether solution is washed with NaHCO$_3$ solution and water, dried and concentrated by evaporation. The crude product obtained as oil (18 g) is chromatographed on a silica gel column once with ethyl acetate/hexane 1:4 and once with CH$_2$Cl$_2$+1% of methanol. Yield of product (oil): 3 g (16.8%).

C$_{24}$H$_{30}$O$_6$S: calculated: C, 64.55; H, 6.77; S, 7.18%. (446.56): found: C, 64.4; H, 6.7; S, 7.2%.

EXAMPLE 14

2-(Diethoxyacetyl)-dibenzothiophene 6.5 g (0.1 mole) of NOCl is introduced at 5°–10° into 8.8 g (0.04 mole) of 2-acetyl-dibenzothiophene suspended in 160 ml of ethanol, and a yellow reaction solution is formed. After removal of the cooling bath, the temperature of the reaction solution rises with the evolution of HCl; the temperature is held at 35° by slight cooling. After further stirring for 4 hours at room temperature, the reaction solution is concentrated by evaporation, and the residue is taken up in ether. The ether solution is washed with NaHCO$_3$ solution and water, dried and then concentrated by evaporation. The crude product (oil) is chromatographed on a silica gel column with CH$_2$Cl$_2$.

Yield of product (oil): 5.4 g (43%).

C$_{18}$H$_{18}$O$_3$S: calculated: C, 68.77; H, 5.77; S, 10.20%. (314.40): found: C, 68.8; H, 5.6; S, 10.2%.

EXAMPLE 15

0.1 g in each case of a photoinitiator according to the invention is dissolved in 10.0 g of freshly distilled methyl acrylate. This solution is irradiated, in a thermostatically controlled water bath at 25°, in a quartz glass tube of 1.5 cm diameter with a high-pressure mercury vapour lamp. The lamp is at a distance of 10 cm from the quartz tube. Before irradiation, nitrogen is passed for 1 minute through the solution of the initiator, and also during irradiation the passing through of nitrogen is continued. The polymerisation commencing during irradiation manifests itself by an increase in temperature of the irradiated solution. The irradiation time until the temperature rise in the solution occurs is recorded as starting time; the total irradiation time is 20 seconds. Immediately after irradiation, the irradiated solution is cooled in order to prevent a thermal polymerisation. The solution of the formed polmer in the monomer is rinsed with small amounts of ethyl acetate in a round-bottomed flask, and subsequently the solvent and the unpolymerised monomeric fraction are distilled off in a rotary evaporator. The polymeric residue is dried in a vacuum-drying cabinet at 50°–60° and then weighed.

The values obtained with the photoinitiators according to the invention using the test method described above are given in the following Table I.

TABLE I

| Photoinitiator | Starting time in sec. | Amount of formed polymethyl acrylate |
|---|---|---|
| compound from Example 1 | 8 | 5,4% |
| compound from Example 2 | 6 | 6,8% |
| compound from Example 3 | 6 | 7,2% |
| compound from Example 4 | 9 | 3,4% |
| compound from Example 5 | 6 | 6,7% |
| compound from Example 6 | 5 | 6,2% |

Without photoinitiator, the amount of polymer is below 0.1% and no rise in temperature occurs during irradiation.

EXAMPLE 16

A resin mixture of 80 parts of Plex 6617 (acrylate resin from the firm Röhm, Darmstadt) and 20 parts of trimethylolpropane tris-acrylate is mixed with 2 parts in each case of a photoinitiator according to the invention, and the mixture is spread, in a thickness of 40 μm, onto glass plates using a film spreader. These films are exposed to the air for about 20 seconds and subsequently irradiated with a medium-pressure Hg vapour lamp (Hanovia-Gerät, Model 45080). During irradiation, the specimens are moved on a conveyor belt under the UV lamp at such a rate that the effective exposure time is 0.16 seconds per pass. In the following Table II are given the number of passes (D) which were necessary to obtain rub-fast films with the photoinitiators according to the invention. Furthermore, the hardness of the film was determined using a König pendulum apparatus.

TABLE II

| Photoinitiator | Passes necessary to to attain fastness to rubbing | König pendulum hardness as a function of the number of passes |
|---|---|---|
| compound from Example 1 | 12 | 50(10D); 101(12D) |
| compound from Example 4 | 10 | 95(9D); 102(10D) |
| compound from Example 5 | 8 | 111(8D); 125(10D); 127(12D) |
| compound from Example 6 | 9 | 94(9D); 115(11D); 133(13D) |
| compound from Example 7 | 6 | 87(6D); 107(8D); 116(10D) |
| compound from Example 8 | 10 | 143(10D); 162(12D); 158(14D) |
| compound from Example 9 | 8 | 127(8D); 156(10D); 156(12D) |
| compound from Example 10 | 9 | 142(9D); 162(11D) |
| compound from Example 11 | 8 | 123(8D); 152(10D); 146(12D) |
| compound from Example 12 | 11 | 21(11D); 51(13D); 38(15D) |
| compound from Example 13 | 10 | 25(10D); 46(12D); 53(14D) |
| compound from Example 14 | 10 | 133(10D); 137(12D); 141(14D) |

EXAMPLE 17

In order to determine the degree of surface drying, lacquers of compositions given in Example 16 are applied in a thickness of 15 μm to special cardboard. The specimens are cured in 3 passes with the same irradiation apparatus as described in Example 16. After a brief intermediate standing period, the specimens are treated with talcum, and subsequently the gloss is measured. High gloss values indicate a rapid surface drying. With the compound of Example 5, the gloss value obtained is 79.1%, with the compound of Example 6 the gloss value is 83.7% and with the compound of Example 7 the gloss value is 79%.

We claim:

1. A photopolymerizable system comprising at least one unsaturated photopolymerizable compound and 0.1 to 20% by weight of a compound of the formulae I or II

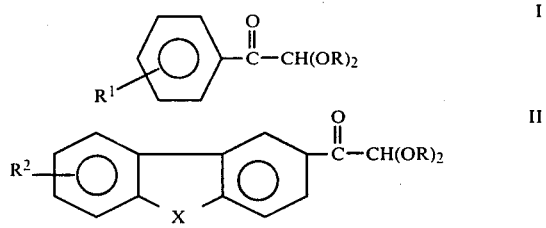

wherein

X represents oxygen or sulphur,

R represents alkyl having 1–4 C atoms, alkoxyalkyl having 3–6 C atoms, $C_1$–$C_4$-alkyl-$OCH_2$—$CH_2OCH_2CH_2$ or chloroalkyl having 2–3 C atoms, $R^1$ represents alkyl having 1–4 C atoms, alkoxy or alkylthio having 1–4 C atoms, cycloalkyl having 5–6 C atoms, aralkyl having 7–9 C atoms, chlorine, bromine, a group of the formula —CO—CH(OR)$_2$, or a group of the formula

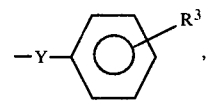

Y represents a direct bond, oxygen or sulphur, $R^2$ represents hydrogen, alkyl having 1–4 C atoms, alkoxy or alkylthio having 1–4 C atoms, chlorine, bromine or a group —CO—CH(OR)$_2$, and $R^3$ represents hydrogen, alkyl having 1–4 C atoms, alkoxy having 1–4 C atoms, chlorine, bromine, alkoxycarbonyl having 2–5 C atoms, or a group of the formula —CO—CH(OR)$_2$ as a photoinitiator.

2. A photopolymerizable system according to claim 1 wherein the photoinitiator is a compound of the formula I wherein R represent alkyl having 1–4 C atoms or alkoxyalkyl having 3–4 C atoms, and $R^1$ represents alkyl having 1–4 C atoms, alkoxy having 1–4 C atoms, chlorine, a group of the formula —CO—CH(OR)$_2$, or a group of the formula

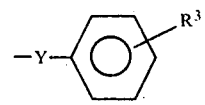

wherein Y represents a direct bond, oxygen or sulphur, and $R^3$ represent H, $CH_3$, Cl or $-CO-CH(OR)_2$.

3. A photopolymerizable system according to claim 1 wherein the photoinitiator is a compound of the formula I, wherein R represent alkyl having 1-4 C atoms, and $R^1$ represents methyl, methoxy, chlorine, a group of the formula $-CO-CH(OR)_2$, or a group of the formula

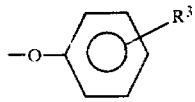

wherein $R^3$ represents hydrogen or $-CO-CH(OR)_2$.

4. A photopolymerizable system according to claim 1 wherein the photoinitiator is a compound of the formula I, wherein R represents alkyl having 1-4 C atoms, and $R^1$ represents methyl, methoxy, a group of the formula $-CO-CH(OR)_2$, or a group of the formula

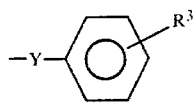

wherein $R^3$ represents hydrogen or $-CO-CH(OH)_2$, and Y represents a direct bond, oxygen or sulphur.

5. A photopolymerizable system according to claim 1 wherein the photoinitiator is a compound of the formula II, wherein X represents oxygen or sulphur, R represents alkyl having 1-4 C atoms or alkoxyalkyl having 3-4 C atoms, and $R^2$ represents hydrogen, alkyl having 1-4 C atoms, alkoxy having 1-4 C atoms, chlorine or $-CO-CH(OR)_2$.

6. A photopolymerizable system according to claim 1 wherein the photoinitiator is a compound of the formula II wherein X represents oxygen, R represents alkyl having 1-4 C atoms, and $R^2$ represents hydrogen or $-CO-CH(OR)_2$.

7. A photopolymerizable system according to claim 1 wherein the photoinitiator is a compound of the formula II, wherein X represents oxygen or sulphur, R represents alkyl having 1-4 C atoms, and $R^2$ represents hydrogen.

8. A photopolymerizable system according to claim 1 wherein the photoinitiator is 4-diisopropoxyacetyl diphenyl oxide.

9. A photopolymerizable system according to claim 1 wherein the photoinitiator is 4,4'-bis-(dimethoxyacetyl)-diphenyl oxide.

10. A photopolymerizable system according to claim 1 wherein the photoinitiator is 4-diethoxyacetyl anisole.

11. A photopolymerizable system according to claim 1 wherein the photoinitiator is 2-diethoxyacetyl diphenyl oxide.

12. A photopolymerizable system comprising at least one unsaturated photopolymerizable compound and 0.1 to 20% by weight of 4,4'-bis-(diethoxyacetyl)-diphenyl oxide.

13. Photopolymerisable system according to claim 1, which system is a lacquer or a printing ink.

* * * * *